United States Patent [19]

Hite et al.

[11] Patent Number: 5,028,629

[45] Date of Patent: Jul. 2, 1991

[54] 5-LIPOXYGENASE INHIBITORS

[75] Inventors: Gary A. Hite; Edward D. Mihelich, both of Indianapolis; Tulio Suarez, Greenwood, all of Ind.

[73] Assignee: Eli Lilly and Company, Indianapolis, Ind.

[21] Appl. No.: 500,820

[22] Filed: Mar. 28, 1990

[51] Int. Cl.$^5$ .................. C07J 83/10; A61K 31/165; A61K 31/185

[52] U.S. Cl. ..................... 514/575; 562/621

[58] Field of Search .................. 562/621; 514/575

[56] References Cited

U.S. PATENT DOCUMENTS

| | | | |
|---|---|---|---|
| 3,671,580 | 6/1972 | Shen et al. | 260/520 |
| 4,604,407 | 8/1986 | Haslanger et al. | 514/575 |
| 4,608,390 | 8/1986 | Summers | 562/621 |
| 4,623,661 | 11/1986 | Summers | 562/621 |
| 4,705,782 | 11/1987 | Logan et al. | 562/621 |
| 4,738,986 | 4/1988 | Kneen et al. | 562/621 |
| 4,820,828 | 4/1989 | Demers et al. | 562/621 |

FOREIGN PATENT DOCUMENTS

| | | |
|---|---|---|
| 0161939 | 11/1985 | European Pat. Off. |
| 0196184 | 10/1986 | European Pat. Off. |
| 1444492 | 7/1976 | United Kingdom |
| 2196629 | 5/1988 | United Kingdom |

OTHER PUBLICATIONS

Summers, et al., *J. Med. Chem.*, 30, (3, 574–580 (1987).
Jackson et al., *J. Med. Chem.*, 31, (3), 499–500 (1988).
Tateson et al., *Br. J. Pharmacol.*, 94, 528–539 (1988).
Summers et al., *J. Med. Chem.*, 31, (10), 1960–1964 (1988).
Summers et al., *J. Med. Chem.*, 31(1), 3–5 (1988).
Choudhary et al., *J. Chem. Eng. Data*, 30, 237–239 (1985).
Kehl et al., *Arzneim.-Forsch./Drug Res.*, 28 (11), 2087–2092 (1978).
Summers et al., *J. Med. Chem.*, 30, (11), 2121–2126 (1987).

Primary Examiner—J. E. Evans
Attorney, Agent, or Firm—John C. Demeter; Leroy Whitaker

[57] ABSTRACT

This invention relates to 2-(substituted)-N-hydroxy-N-alkylcinnamamides of the formula:

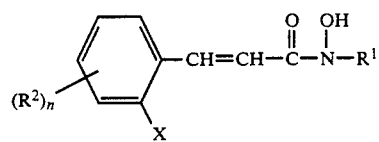

where
$R^1$ is $C_1$–$C_4$ alkyl;
n is 0 or 1;
$R^2$ is trifuloromethyl, $C_1$–$C_{10}$ alkyl, phen($C_1$–$C_4$)alkylene or

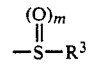

where m is 0, 1 or 2 and $R^3$ is $C_1$–$C_4$ alkyl;
X is $C_1$–$C_6$ alkyl, phenyl, phen($C_1$–$C_4$)alkylene where the phenyl ring is unsubstituted or monosubstituted with —S(O)$_m$—$R^3$ and m and $R^3$ are as defined above, or

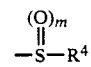

where m is 0, 1 or 2 and $R^4$ is $C_2$–$C_{12}$ alkenyl, $C_2$–$C_{12}$ alkynyl, or unsubstituted or monosubstituted $C_1$–$C_{20}$ alkyl where the substituent is $CF_3$, $C_3$–$C_8$ cycloalkyl, or phenyl, or a pharmaceutically acceptable salt thereof; formulations containing those compounds and methods of using such compounds as 5-lipoxygenase inhibiting agents.

24 Claims, No Drawings

5-LIPOXYGENASE INHIBITORS

BACKGROUND OF THE INVENTION

This invention relates to certain 2-substituted-N-hydroxy-N-alkylcinnamamides, compositions containing those compounds and methods of their use.

The enzyme 5-lipoxygenase (5-LO) catalyzes the first step of a biochemical synthesis pathway by which arachidonic acid is converted into leukotrienes. Numerous and extremely potent biological activities have been associated with leukotrienes. Leukotrienes have been implicated as important mediators in a variety of disease states such as asthma, arthritis, psoriasis and allergy.

Considerable efforts have been directed toward the control of leukotrienes by means of leukotriene antagonists or by control of leukotriene biosynthesis. Generally, research efforts directed toward the control of leukotriene biosynthesis have been directed toward the discovery of inhibitors of the 5-LO pathway and, in particular, 5-LO specific inhibitors.

The principle focus of 5-LO inhibitor research efforts have been directed toward hydroxamic acid derivatives. Hydroxamic acid containing molecules rank among the most potent known in vitro inhibitors of 5-LO.

In U.K. Patent Application GB 2,196,629 certain ring substituted-N-hydroxy-N-substituted benzamide and cinnamamide compounds are disclosed as antileukotriene agents. The ring substituent may be a group having the Formula (Ra)(Rb) C=CH— where (Ra)(Rb)C= is an unsaturated aliphatic hydrocarbylene group containing 3 to 19 carbon atoms; a group having the Formula $R_3$—C≡C— where $R_3$ is a hydrogen atom or a saturated or unsaturated aliphatic hydrocarbyl group containing 1 to 18 carbon atoms; or a group having the Formula $R_4$—S— where $R_4$ is an aliphatic hydrocarbyl group containing 1 to 20 carbon atoms. The N-substituent may be a $C_1$-$C_6$ alkyl group, a $C_3$-$C_7$ cycloalkyl group or a substituted or unsubstituted aryl group.

In European Patent Application 0196184 certain aryl compounds are disclosed which include, among many others, certain cinnamohydroxamic acid analogs.

Neither of the above two references contain any recognition of the importance of a 2-position substituent on a cinnamohydroxamic acid skeleton.

Unfortunately, many of the known compounds suffer from toxicity problems, lack of bioavailability or are short lived in vivo. The hydroxamic acid group is rapidly metabolized to the corresponding, and inactive, carboxylic acid, particularly after oral administration. It was surprisingly discovered that the compounds of the present invention, as defined herein, are particularly advantageous inhibitors of 5-LO and have useful medical prophylactic and therapeutic properties. The compounds of the present invention and their pharmaceutically acceptable salts possess surprisingly high potency.

The compounds of the present invention differ from known compounds primarily by the requirement for an alkenyl bridge between the phenyl ring and the hydroxamic acid group as well as the requirement for a 2-position substituent on the phenyl ring. The unexpected and surprising advantages of the compounds of the present invention are believed at least in part to be a consequence of the alkenyl bridge and/or the type and position of substituents on the phenyl ring.

Accordingly, it is a primary object of the present invention to provide novel 2-substituted-N-hydroxy-N-alkyl cinnamamides which are potent selective 5-LO inhibitors and useful in the treatment of asthma and allergic diseases, inflammatory bowel disease, psoriasis, shock, adult respiratory distress syndrome (ARDS) and arthritis.

A further object of the present invention is to provide therapeutic compositions for treating said diseases and disorders.

Still another object is to provide methods for treating said diseases and disorders.

Other objects, features and advantages will become apparent to those skilled in the art from the following description and claims.

SUMMARY OF THE INVENTION

The present invention provides novel 2-(substituted)-N-hydroxy-N-alkylcinnamamides of the Formula

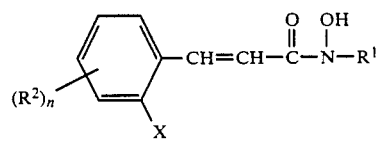

where $R^1$ is $C_1$-$C_4$ alkyl;

n is 0 or 1;

$R^2$ is trifluoromethyl, $C_1$-$C_{10}$ alkyl, phen($C_1$-$C_4$)alkylene or

where m is 0, 1 or 2 and $R^3$ is $C_1$-$C_4$ alkyl;

X is $C_1$-$C_6$ alkyl, phenyl, phen($C_1$-$C_4$)alkylene where the phenyl ring is unsubstituted or monosubstituted with —S(O)$_m$—$R^3$ and m and $R^3$ are as defined above, or

where m is 0, 1 or 2 and $R^4$ is $C_2$-$C_{12}$ alkenyl, $C_2$-$C_{12}$ alkynyl, or unsubstituted or monosubstituted $C_1$-$C_{20}$ alkyl where the substituent is $CF_3$, $C_3$-$C_8$ cycloalkyl, or phenyl, or a pharmaceutically acceptable salt thereof.

In addition to the compounds of Formula I, the present invention provides pharmaceutical formulations comprising a compound of Formula I in association with a pharmaceutically acceptable carrier, diluent or excipient.

The present invention also provides a method of treating asthma, allergic diseases, inflammatory bowel disease, psoriasis, shock, ARDS or arthritis in mammals comprising administering to a mammal in need of such treatment an effective amount of a compound according to Formula I.

DETAILED DESCRIPTION OF THE INVENTION

The term "alkyl" by itself or as part of another substituent, unless otherwise stated includes straight or branched chain groups such as methyl, ethyl, n-propyl, isopropyl, n-butyl, t-butyl, isobutyl, sec-butyl, neopentyl and the like and where indicated higher homologs and isomers such as n-octyl, isooctyl and the like.

The term "phen($C_1$–$C_4$) alkylene" as employed herein includes benzyl, 2-phenylethyl, 3-phenylpropyl, and 4-phenylbutyl.

The term "$C_2$–$C_{12}$ alkenyl" as employed herein includes an unsaturated hydrocarbon group having from 2 to 12 carbon atoms and a single carbon-carbon double bond such as ethenyl, 1-propenyl, 2-propenyl, 1-butenyl, 2-butenyl and the like.

The term "$C_2$–$C_{12}$ alkynyl" as employed herein includes an unsaturated hydrocarbon group having from 2 to 12 carbon atoms and a single carbon-carbon triple bond such as ethynyl, 1-propynyl, 1-butynyl and the like.

The following compounds illustrate compounds contemplated within the scope of Formula I:

2-methylthio-6-n-hexyl-N-hydroxy-N-methylcinnamamide
2-(1-but-3-enylthio-N-hydroxy-N-methylcinnamamide
2-n-hexylthio-N-hydroxy-N-methylcinnamamide
2-n-butyl-N-hydroxy-N-methylcinnamamide
2-[1-(3-trifluoromethylpropyl)thio]-N-hydroxy-N-methylcinnamamide
2-methylthio-4-(3-phenylpropyl)-N-hydroxy-N-methylcinnamamide
2-n-butylthio-4-trifluoromethyl-N-hydroxy-N-methylcinnamamide
2-n-butyl-4-methylthio-N-hydroxy-N-methylcinnamamide
2-methylsulfonyl-5-n-hexyl-N-hydroxy-N-methylcinnamamide
2-methylsulfinyl-4-n-hexyl-N-hydroxy-N-methylcinnamamide
2-methylsulfinyl-5-n-hexyl-N-hydroxy-N-methylcinnamamide
2-benzyl-4-methylsulfonyl-N-hydroxy-N-methylcinnamamide
2-benzyl-4-methylthio-N-hydroxy-N-methylcinnamamide
2-(4-methylthiobenzyl)-N-hydroxy-N-methylcinnamamide
2-(4-methylsulfonylbenzyl)-N-hydroxy-N-methylcinnamamide
2-methylsulfonyl-4-(3-phenylpropyl)-N-hydroxy-N-methylcinnamamide
2-methylthio-3-n-hexyl-N-hydroxy-N-methylcinnamamide
2-tert-butylthio-N-hydroxy-N-methyl-cinnamamide
2-methylthio-4-n-hexyl-N-hydroxy-N-methylcinnamamide
2-methylsulfinyl-3-n-hexyl-N-hydroxy-N-methylcinnamamide
2-methylsulfonyl-3-n-hexyl-N-hydroxy-N-methylcinnamamide
2-methylsulfonyl-4-n-hexyl-N-hydroxy-N-methylcinnamamide
2-methylthio-N-hydroxy-N-methyl-cinnamamide
2-phenyl-N-hydroxy-N-methylcinnamamide
2-[1-(2-phenylethyl)thio]-N-hydroxy-N-methyl-cinnamamide
2-cyclohexylmethylthio-N-hydroxy-N-methylcinnamamide
2-methylthio-5-(3-phenylpropyl)-N-hydroxy-N-methylcinnamamide
2-n-butylthio-5-(3-phenylpropyl)-N-hydroxy-N-methylcinnamamide
2-ethyl-5-(3-phenylpropyl)-N-hydroxy-N-methylcinnamamide
2-benzylthio-N-hydroxy-N-methyl-cinnamamide
2-methylsulfinyl-4-(3-phenylpropyl)-N-hydroxy-N-methylcinnamamide
2-n-butylthio-N-hydroxy-N-methylcinnamamide
2-n-butylsulfonyl-N-hydroxy-N-methylcinnamamide
2-[1-(3-phenylpropyl)thio]-N-hydroxy-N-methylcinnamamide
2-n-butylsulfinyl-N-hydroxy-N-methylcinnamamide
2-benzyl-N-hydroxy-N-methylcinnamamide
2-n-octylthio-N-hydroxy-N-methylcinnamamide
2-[1-0(6-phenylhexyl)thio]-N-hydroxy-N-methylcinnamamide
2-[1-(2-methylpropyl)thio]-N-hydroxy-N-methylcinnamamide
2-methylsulfinyl-5-(3-phenylpropyl)-N-hydroxy-N-methylcinnamamide
2-methylsulfonyl-5-(3-phenylpropyl)-N-hydroxy-N-methylcinnamamide
2-n-butylthio-N-hydroxy-N-isopropylcinnamamide
2-(3-phenylpropyl)-N-hydroxy-N-methylcinnamamide
2-[1-(5-trifluoromethylpentyl)thio]-N-hydroxy-N-methylcinnamamide
2-methylthio-5-n-hexyl-N-hydroxy-N-methylcinnamamide
2(2-propargylthio)-N-hydroxy-N-methylcinnamamide Preferred compounds of Formula I are those where:
$R^1$ is $C_1$–$C_3$ alkyl;
n is 0 or 1;
$R^2$ is $CF_3$, phen($C_1$–$C_4$)alkylene, or —S—$R^3$ and $R^3$ is $C_1$–$C_4$ alkyl;
X is $C_3$–$C_6$ alkyl, phen($C_1$–$C_4$)alkylene, where the phenyl ring is unsubstituted or S—$R^4$ and $R^4$ is $C_3$–$C_6$ alkenyl, unsubstituted or substituted $C_1$–$C_{10}$ alkyl where the substituent is $CF_3$, $C_5$–$C_6$ cycloalkyl, or phenyl, or a pharmaceutically acceptable salt thereof.

More preferred compounds of Formula I are those where:

$R_1$ is methyl or isopropyl;
n is 0 or 1;
$R^2$ is a 4- or 3-position $CF_4$, phen($C_1$–$C_3$)alkylene, or —S—$R^3$ where $R^3$ is $C_1$–$C_3$ alkyl;
X is phen($C_1$–$C_3$)alkylene or —S—$R^4$ where $R^4$ is $C_3$–$C_6$ alkenyl, unsubstituted or substituted $C_1$–$C_{10}$ alkyl where the substituent is $CF_3$, cyclohexyl, or phenyl, or a pharmaceutically acceptable salt thereof.

Particularly preferred compounds of Formula I are those where:
$R^1$ is methyl or isopropyl;
n is 0 or 1;
$R^2$ is a 4-position phen($C_1$–$C_3$)alkylene;
X is —S—$R^4$ is unsubstituted or substituted $C_1$–$C_8$ alkyl where the substituent is phenyl, or a pharmaceutically acceptable salt thereof.

The compounds of the present invention or their precursors can be prepared according to the following processes.

Process 1

Step 1:

-continued

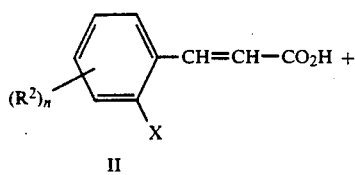
II

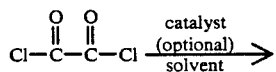

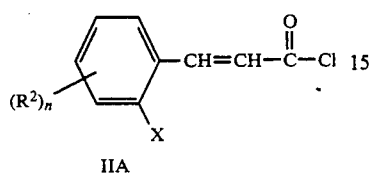
IIA

Step 2:

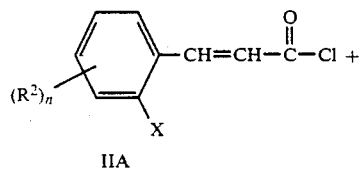
IIA

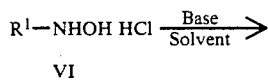
VI

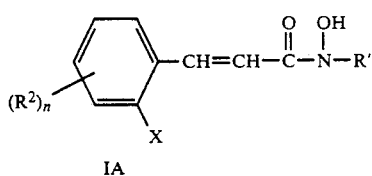
IA where $R_1$, n and X are as defined above for Formula I with the exception of those compounds where X is $S(O)_m$—$R^4$ and m is one or two (i.e., sulfinyl and sulfonyl).

In Process 1, a 2-substituted cinnamic acid of Formula II is reacted with oxalyl chloride in the presence or absence of a catalyst in an inert or substantially inert solvent or mixture of solvents to afford the corresponding cinnamic acid chloride of Formula IIA which can be isolated or further reacted with a hydroxylamine salt of Formula VI in the presence of a base in an inert or substantially inert solvent or mixture of solvents to afford the desired compound of Formula IA.

Suitable solvents for use in Step 1 of the above process are haloalkanes and methylene chloride is preferred.

When a catalyst is used for the Process 1, Step 1 reaction, preferably it is dimethylformamide (DMF).

The Process 1, Step 1 reaction can be carried out at temperatures between about −30° C. and about 30° C. Preferably, this reaction is carried out between about −10° C. and about 10° C.

Suitable solvents for use in the Process 1, Step 2 reaction are ethers and preferably tetrahydrofuran.

Suitable bases for use in the Process 1, Step 2 reaction include tertiary amines and preferably triethylamine.

The Process 1, Step 2 reaction can be carried out at temperature between about −20° C. and about 50° C.

Preferably, the reaction is carried out between about −5° C. and about 30° C.

In Process 1, Step 1 approximately 1½ equivalents of oxalyl chloride is used per equivalent of 2-substituted cinnamic acid. In Process 1, Step 2, about 2 equivalents of the hydroxylamine salt of Formula VI is used per equivalent of the 2-substituted cinnamic acid chloride of Formula IIA. The amount of base used is in excess of the amount of hydroxylamine salt of Formula VI.

For those compounds of Formula I where X contains a sulfinyl or sulfonyl group bonded to the phenyl ring, the compounds of Formula IA are further reacted with oxone in a suitable alcohol solvent, preferably methanol, at a temperature of from about −10° C. to about 50° C. The amount of oxone used in relationship to the amount of 2-substituted cinnamamide of Formula IA and the length of time the reaction is allowed to proceed will, of course, dictate whether the sulfinyl or sulfonyl derivatives are afforded.

The compounds of Formula II are prepared according to the following two processes.

Process 2

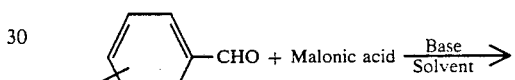

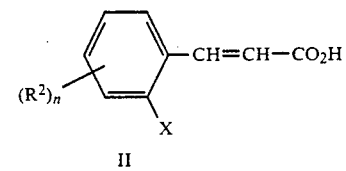
II

Process 3

Step 1:

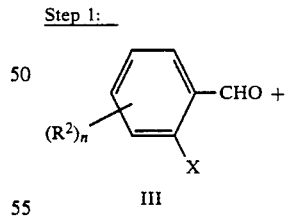
III

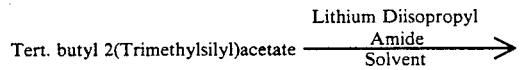

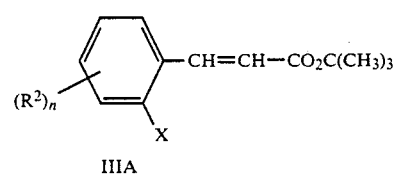
IIIA

Step 2:

-continued

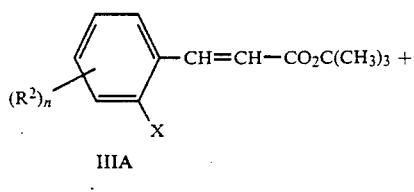
IIIA trifluoroacetic acid $\xrightarrow{\text{solvent}}$

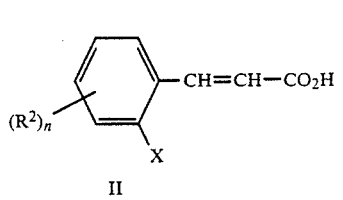
II

In Process 2 a 2-substituted benzaldehyde of Formula III is reacted with malonic acid in the presence of a base in an inert or substantially inert solvent or mixture of solvents to afford a 2-substituted cinnamic acid of Formula II which can be isolated or further reacted according to Process 1.

The preferred solvent for this reaction is pyridine. Suitable bases are disubstituted amines and preferably piperidine. Only a small amount of base is preferably used in this reaction. About 3 equivalents of malonic acid per equivalent of the 2-substituted benzaldehyde of Formula III are used in this reaction. Temperatures for Process 2 will range from about 110° C. to about 120° C.

In Process 3, a 2-substituted benzaldehyde of Formula III is reacted with tertiary butyl 2-(trimethylsilyl-)acetate in the presence of lithium diisopropylamide in an inert or substantially inert solvent or mixture of solvents to afford a tertiary butyl 2-substituted cinnamate of Formula IIIA which may be isolated or further reacted with trifluoroacetic acid in a suitable inert or substantially inert solvent or mixture of solvents to afford a 2-substituted cinnamic acid of Formula II.

Suitable solvents for the Process 3, Step 1 reaction generally are ethers and preferred is tetrahydrofuran. Generally, the temperature for the Step 1, Process 3, reaction is from about −60° C. to about −20° C. and preferably from about −50° C. to about −30° C. Suitable solvents for the Step 2 reaction of Process 3 include haloalkanes and preferred is methylene chloride. Suitable temperatures for the Step 2 reaction are generally from about 35° C. to about 45° C.

The compounds of Formula III are prepared according to the following two processes:

Process 4

Step 1:

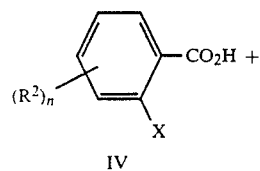
IV

Lithium Aluminum Hydride $\xrightarrow{\text{solvent}}$

-continued

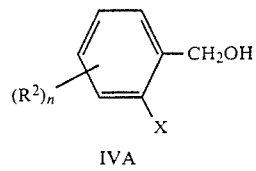
IVA

Step 2:

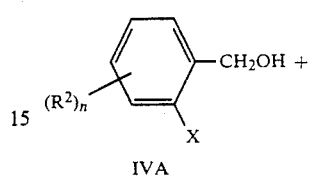
IVA

Pyridinium dichromate $\xrightarrow{\text{solvent}}$

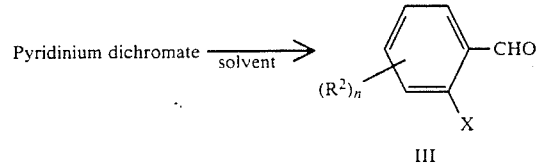
III

Process 5

Step 1:

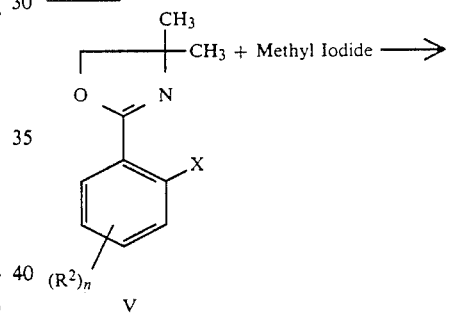
V

+ Methyl Iodide $\longrightarrow$

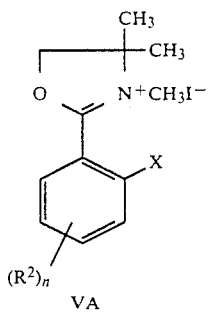
VA

Step 2:

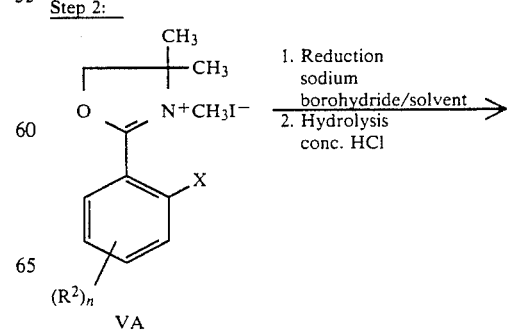
VA

1. Reduction sodium borohydride/solvent
2. Hydrolysis conc. HCl
$\longrightarrow$

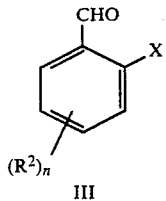

In Process 4, Step 1, a 2-substituted benzoic acid of Formula IV is reduced with lithium aluminum hydride in a suitable inert or substantially inert solvent or mixture of solvents to afford the corresponding alcohol of Formula IVA which may be isolated or further reacted with pyridinium dichromate in a suitable inert or substantially inert solvent or mixture of solvents to afford a 2-substituted benzaldehyde of Formula III.

Suitable solvents for the Process 4, Step 1 reaction are generally ethers and preferred is diethyl ether. Suitable solvents for the Process 4, Step 2 reaction are generally haloalkanes and preferred is methylene chloride. Temperatures for the Process 4, Step 1 reaction are generally from about −20° C. to about 40° C. Temperatures for the Process 4, Step 2 reaction are generally from about 10° C. to about 40° C. and preferably at about room temperature.

In Process 5, a 2-oxazoline of Formula V is reacted with methyl iodide to afford a quarternized 2-oxazoline of Formula VA which may be isolated or further reacted with sodium borohydride in a suitable inert or substantially inert solvent or mixture of solvents and then hydrolyzed with 3N HCl to afford a 2-substituted benzaldehyde of Formula III.

An excess of methyl iodide is generally used in the quarternization reaction of Process 5, Step 1. This reaction is generally carried out at about room temperature. The reduction with sodium borohydride, Process 5, Step 2, is generally carried out at from about −10° C. to about 20° C. and the hydrolysis with hydrochloric acid is generally carried out at reflux. Suitable solvents for the reduction reaction include alcohols and preferably ethanol.

The 2-substituted benzoic acids of Formula IV are commercially available or can be prepared from commercially available reactants, such as thiosalicylic acid, by known methods. Alternatively, the 2-substituted benzoic acids of Formula IV can be obtained by hydrolysis of a 2-oxazoline of Formula V using 4.5N HCl where the 2-oxazoline is at a concentration of about 0.05 M at reflux.

The 2-oxazolines of Formula V are prepared by reacting benzoic acid, bromobenzoic acid, anisic acid or other suitably substituted benzoic acid with 2-amino-2-methyl-1-propanol. To the extent a particular X or $R^2$ substituent as defined for Formula IA is not already present on the phenyl ring, the desired substituent at a desired position can be effected through reactions which are apparent and well known to those skilled in the art. Such reactions include, but are not limited to, alkylation, Grignard addition or coupling and silation/desilation, including combinations of such reactions. The conditions for such reactions are well known or readily ascertained by those skilled in the art. For example, treatment of 2-phenyloxazoline with butyllithium followed by alkylation with dimethyldisulfide affords an ortho methylthio substituent on the phenyl ring. The 2-(2-methylthiophenyl)oxazoline may then be hydrolyzed to a 2-methylthiobenzoic acid or 2-methylthiobenzaldehyde in accordance with reactions described above.

The phrase "inert or substantially inert solvents" are substances that provide a medium in which a reaction will occur but otherwise do not materially contribute to the reaction.

Modifications to the above processes may be necessary to accommodate reactive functionalities of particular substituents. Such modifications would be both apparent and known to those skilled in the art.

By virtue of their hydroxamic acid moiety, the compounds of Formula I include the pharmaceutically acceptable base addition salts thereof. Such salts include those derived from inorganic bases, such as alkali or alkaline earth metal hydroxides, and the like. Such bases useful in preparing the salts of this invention thus include sodium hydroxide, potassium hydroxide, calcium hydroxide and the like. The potassium and sodium salt forms are particularly preferred.

It is recognized that various isomeric forms of the compounds of Formula I may exist. This invention is not limited to any particular isomer, but rather includes all possible individual isomers and mixtures thereof. The compound of Example 1 was obtained in the Z configuration; all other examples were obtained in the E configuration.

The pharmaceutically acceptable salts embraced by Formula I of the present invention are prepared by reacting an equimolar or excess amount of a metal hydroxide, with a compound of Formula I in a suitable mutual solvent such as water and alcohols, such as methanol, ethanol, isopropanol and the like. The particular choice of solvent will depend on the relative solubilities of the starting materials and the resultant salts, and slurries rather than solutions of certain reagents may be used to obtain the salts. The salt forming reaction is carried out at about −10° C. to about 100° C., preferably at about room temperature, and the solvent is stripped off by conventional means such as a rotary evaporator.

The following examples will further illustrate this invention but are not intended to limit it in any way. In Table I, some compounds of the present invention that have been made are listed. Unless otherwise indicated, the named alkyl groups are linear. Specific illustrated preparation of certain compounds are described after Table I.

TABLE I

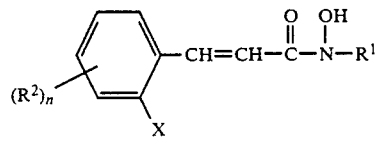

| Ex. No. | $R^1$ | X | $R^2$ | n | M.P. °C. |
|---|---|---|---|---|---|
| 1 | $CH_3$ | $-SCH_3$ | 6-hexyl | 1 | 80-81 |

TABLE I-continued $$\underset{(R^2)_n}{\text{Ar}}\text{CH}=\text{CH}-\overset{O}{\underset{\|}{C}}-\underset{\underset{R^1}{|}}{N}-\overset{OH}{}$$

(phenyl ring with (R²)ₙ and X substituents)

| Ex. No. | R¹ | X | R² | n | M.P. °C. |
|---|---|---|---|---|---|
| 2 | CH₃ | —SCH₂CH₂CH=CH₂ | — | 0 | 66–67 |
| 3 | CH₃ | —S-hexyl | — | 0 | 55.5–57.5 |
| 4 | CH₃ | -butyl | — | 0 | oil |
| 5 | CH₃ | —SCH₂CH₂CH₂CF₃ | — | 0 | oil |
| 6 | CH₃ | —SCH₃ | 4-CH₂CH₂CH₂C₆H₅ | 1 | 113–115 |
| 7 | CH₃ | —S-butyl | 4-CF₃ | 1 | 93–95 |
| 8 | CH₃ | -butyl | 4-SCH₃ | 1 | 102.5–105 |
| 9 | CH₃ | —SO₂CH₃ | 5-hexyl | 1 | 132–133 |
| 10 | CH₃ | —S(O)CH₃ | 4-hexyl | 1 | 154–155 |
| 11 | CH₃ | —S(O)CH₃ | 5-hexyl | 1 | 164–164 |
| 12 | CH₃ | —CH₂C₆H₅ | 4-SO₂CH₃ | 1 | 149–150 |
| 13 | CH₃ | —CH₂C₆H₅ | 4-SCH₃ | 1 | 134–136 |
| 14 | CH₃ | —CH₂C₆H₄-4-SCH₃ | — | 0 | 138–139 |
| 15 | CH₃ | —CH₂C₆H₄-4-SO₂—CH₃ | — | 0 | 137–139 |
| 16 | CH₃ | —SO₂CH₃ | 4-CH₂CH₂CH₂C₆H₅ | 0 | 125–127 |
| 17 | CH₃ | —SCH₃ | 3-hexyl | 1 | oil |
| 18 | CH₃ | —SC(CH₃)₃ | — | 0 | 116–118 |
| 19 | CH₃ | —SCH₃ | 4-hexyl | 1 | 114–115 |
| 20 | CH₃ | —S(O)CH₃ | 3-hexyl | 1 | 147–148 |
| 21 | CH₃ | —SO₂CH₃ | 3-hexyl | 1 | 119–120 |
| 22 | CH₃ | —SO₂CH₃ | 4-hexyl | 1 | 113–115 |
| 23 | CH₃ | —SCH₃ | — | 0 | 90–91 |
| 24 | CH₃ | C₆H₅ | — | 0 | 107–110 |
| 25 | CH₃ | —SCH₂CH₂C₆H₅ | — | 0 | 89–91 |
| 26 | CH₃ | —SCH₂cyclohexyl | — | 0 | 122–126 |
| 27 | CH₃ | —SCH₃ | 5-CH₂CH₂CH₂C₆H₅ | 1 | 103.5–106 |
| 28 | —CH(CH₃)₂ | —S-butyl | — | 0 | 64–65 |
| 29 | CH₃ | —S-butyl | 5-CH₂CH₂CH₂C₆H₅ | 1 | oil |
| 30 | CH₃ | ethyl | 5-CH₂CH₂CH₂C₆H₅ | 1 | oil |
| 31 | CH₃ | —SCH₂C₆H₅ | — | 0 | 94–95 |
| 32 | CH₃ | —S(O)CH₃ | 4-CH₂CH₂C₆H₅ | 1 | 155–158.5 |
| 33 | CH₃ | —S-butyl | — | 0 | 82.5–85 |
| 34 | CH₃ | —SO₂butyl | — | 0 | 110–111 |
| 35 | CH₃ | —SCH₂CH₂CH₂C₆H₅ | — | 0 | 84–87 |
| 36 | CH₃ | —S(O)-butyl | — | 0 |  |
| 37 | CH₃ | —CH₂C₆H₅ | — | 0 | 138–139 |
| 38 | CH₃ | —S-octyl | — | 0 | 71–72 |
| 39 | CH₃ | —S(CH₂)₆C₆H₅ | — | 0 | 87–88 |
| 40 | CH₃ | —SCH₂CH(CH₃)₂ | — | 0 | 85–88 |
| 41 | CH₃ | —S(O)CH₃ | 5-CH₂CH₂CH₂C₆H₅ | 1 | 142–150 |
| 42 | CH₃ | —SO₂CH₃ | 5-CH₂CH₂CH₂C₆H₅ | 1 | oil |
| 43 | CH₃ | —CH₂CH₂CH₂C₆H₅ | — | 0 | oil |
| 44 | CH₃ | —S(CH₂)₅CF₃ | — | 0 | oil |
| 45 | CH₃ | —SCH₃ | 5-hexyl | 1 | 104–105 |
| 46 | CH₃ | —SCH₂C≡CH | — | 0 | 87–88 |

EXAMPLE 1

Preparation of 2-methylthio-6-n-hexyl-N-hydroxy-N-methylcinnamamide.

A. 2-(2-n-hexylphenyl)-4,4-dimethyloxazoline.

To a solution of 2-(2-methoxyphenyl)-4,4-dimethyloxazoline (61.5g, 0.3 mmol) in 1000 ml of dry THF at 0° C. is added n-hexylmagnesiumbromide while keeping the temperature below 5° C. When the addition is finished, the reaction mixture is allowed to warm up to room temperature and stirred overnight. The reaction mixture is poured over a saturated $NH_4Cl$/ice mixture slowly while stirring, then extracted with ethyl acetate. The extracts are washed with water and then brine, and dried over $MgSO_4$ to afford the subtitle compound.

B. 2-methylthio-6-n-hexylbenzaldehyde.

By substantially following the procedures described in Example 45, Steps B, C and D, the subtitle compound is afforded.

C. 2-methylthio-6-n-hexylcinnamic acid.

To a solution of lithium diisopropylamide, afforded by combining 3.4 g of diisopropylamine with 26 ml of n-butyllithium, at −40° C. in THF is added tert-butyl trimethylsilylacetate (8 g, 0.042 mmol) and the mixture stirred for 1 hour. To the reaction mixture is added 2-methylthio-6-n-hexylbenzaldehyde (7.08 g, 0.03 mmol) dropwise and stirred for 2 hours at −40° C. The reaction mixture is allowed to warm to −10° C. and cold 1N HCl poured in. The mixture is extracted with diethyl ether. The extracts are washed with water and then brine, dried over $MgSO_4$ and concentrated to afford tert-butyl 2-methylthio-6-n-hexylcinnamate which is hydrolyzed in methylene chloride with trifluoroacetic acid by refluxing overnight to afford the subtitle compound.

D. 2-methylthio-6-n-hexyl-N-hydroxy-N-methylcinnamamide.

By substantially following the procedures described in Example 45 Step F, the subtitle compound is afforded.

| Elemental Analysis: | C | H | N |
|---|---|---|---|
| Calculated | 66.41 | 8.20 | 4.56 |
| Found | 66.61 | 8.09 | 4.47 |

Mass Spec.: M+(307)

EXAMPLE 3

Preparation of 2-n-hexylthio-N-hydroxy-N-methylcinnamamide.

By substantially following the procedures described below in Example 33 and using the appropriate reactants, the title compound is afforded.

| Elemental Analysis: | C | H | N | S |
|---|---|---|---|---|
| Calculated | 65.49 | 7.90 | 4.77 | 10.93 |
| Found | 65.20 | 7.91 | 4.71 | 11.00 |

Example 6

Preparation of 2-methylthio-4-)3-phenylpropyl)-n-hydroxy-N-methylcinnamamide.

By substantially following the procedures described below in Example 27 and using the appropriate reactants, the title compound is afforded.

| Elemental Analysis: | C | H | N |
|---|---|---|---|
| Calculated | 70.35 | 6.79 | 4.10 |
| Found | 70.30 | 6.69 | 4.17 |

EXAMPLE 8

Preparation of 2-n-butyl-4-methylthio-N-hydroxy-N-methylcinnamamide.

A. 2-(2-n-butyl-4-methylthiophenyl)-4,4-dimethyloxazoline.

To 110 ml of dry THF is added 2-(4-methylthiophenyl)-4,4-dimethyloxazoline (5.0 g, 22.6 mmol) and cooled in a acetonitrile/dry ice bath. To the mixture is added n-buyllithium (16.9 ml of 1.6 M, 27.1 mmol) and the mixture stirred for 2 hours at −45° C. To the reaction mixture is added iodobutane (3.1 ml, 27.1 mmol) and allowed to warm to room temperature overnight. The reaction mixture is poured into 100 ml of saturated $NH_4Cl$. The layers are separated and the aqueous layer is extracted with 500 ml of diethyl ether. The organic phases are combined and dried over $MgSO_4$ to afford the subtitle compound.

By substantially following the procedures described in Example 27, Steps D, E, F, G and H, the compound 2-n-butyl-4-methylthio-N-hydroxy-N-methylcinnamamide is afforded.

EXAMPLE 13

Preparation of 2-benzyl-4-methylthio-N-hydroxy-N-methylcinnamamide.

A. 2-(2-alpha-hydroxybenzyl-4-methylthiophenyl)-4,4-dimethyloxazoline.

To 110 ml of dry THF is added 2-(4-methylthiophenyl)-4,4-dimethyloxazoline (5.0 g, 22.6 mmol) which is then cooled in an acetonitrile/dry ice bath. The compound n-butyllithium (15.5 ml of 1.6 M, 24.8 mmol) is added slowly and the reaction mixture stirred for 2 hours at −45° C. The reaction mixture temperature is lowered to −78° C. and freshly distilled benzaldehyde in 10 ml of THF is added. While maintaining the temperature at −78° C., the reaction mixture is stirred for 2 hours, then allowed to warm to room temperature. The mixture is then poured into 100 ml of saturated $NH_4Cl$. The layers are separated and the aqueous layer extracted with 500 ml of diethyl ether. The organic layers are combined and washed with brine, then dried over $MgSO_4$ to afford the subtitle compound.

B. 2-(2-benzyl-4-methylthiophenyl)-4,4-dimethyl oxazoline.

Sodium borohydride pellets (4.04 g, 5/16" tablets are added to trifluoroacetic acid (89 ml) placed under nitrogen and cooled in an ice bath. Added dropwise in 45 ml of $CH_2Cl_2$ is 2-(2-alpha-hydroxybenzyl-4-methylthiophenyl)-4,4-dimethyloxazoline and the reaction mixture is stirred overnight at room temperature. An additional 1 g of $NaBH_4$ is added and the reaction mixture is stirred overnight. The reaction mixture is poured into 500 ml of water and neutralized with 50% weight/weight $NaOH/H_2O$ solution, and extracted with diethyl ether. The extract is washed four times with water, then washed with brine and dried over $MgSO_4$ to afford the subtitle compound.

C. 2-benzyl-4-methylthio-N-hydroxy-N-methylcinnamamide.

By substantially following the procedures described for Example 27, Steps D, E, F, G and H, the subtitle compound is afforded.

| Elemental Analysis: | C | H | N | S |
|---|---|---|---|---|
| Calculated | 68.9 | 6.11 | 4.47 | 10.23 |
| Found | 68.69 | 5.87 | 4.39 | 10.04 |

EXAMPLE 17

Preparation of 2-(methylthio)-3-n-hexyl-N-hydroxy-N-methylcinnamamide.

A. 2-(3-n-hexylphenyl)-4,4-dimethyloxazoline.

The subtitle compound is prepared substantially according to the procedures described in Example 45, Step A.

B. 2-(2-trimethylsilyl-5-n-hexylphenyl)-4,4-dimethyloxazoline.

To THF is added 2-(3-n-hexylphenyl)-4,4dimethyloxazoline (58 g, 0.223 mmol) and the mixture cooled to −40° C. To this cooled solution is added dropwise sec-butyllithium (185 ml, 0.2 mmol) and the resulting reaction mixture stirred for ½ hour. To the reaction mixture is added trimethylsilyl chloride (30.5 ml) at −40° C. and the reaction mixture stirred for 2 hours and then allowed to warm to 0°–5° C. The reaction mixture is poured into saturated $NH_4Cl$ and then extracted with diethyl ether. The extracts are washed with water and then with brine, dried over $MgSO_4$ and concentrated to afford the subtitle compound.

C. 2-(2-methylthio-3-n-hexyl-6-trimethylsilylphenyl)-4,4-dimethyloxazoline.

To THF (250 ml) is added 2-(2-trimethylsilyl-5-n-hexylphenyl)-4,4-dimethyloxazoline (72 g) and at −40° C. sec-butyllithium (190 ml) is added. The reaction mixture is stirred for 2 hours and dimethyldisulfide (23.5g) in THF is added dropwise. The reaction mixture is stirred for 2 hours and then poured into saturated $NH_4Cl$ and extracted with diethyl ether. The extracts are washed with water and then brine, dried over $MgSO_4$ and concentrated to afford the subtitle compound.

D. 2-(2-methylthio-3-n-hexylphenyl)-4,4-dimethyloxazoline.

To 100 ml of DMF with 10 ml of water is added (2-methylthio-3-n-hexyl-6-trimethylsilylphenyl)-4,4-dimethyloxazoline and 20 g of tetrabutylammonium fluoride and refluxed overnight. The reaction mixture is cooled and then poured into water and extracted with diethyl ether. The extracts are washed with water and then brine, dried over $MgSO_4$, and concentrated to afford the subtitle compound.

E. 2-methylthio-3-n-hexylbenzaldehyde.

To excess iodomethane is added 2-(2-methylthio-3-n-hexylphenyl)-4,4-dimethyloxazoline and stirred at room temperature overnight to afford 2-(2-methylthio3-n-hexylphenyl)-4,4-dimethyloxazoline methiodide.

The excess iodomethane is stripped off and the methiodide dissolved in ethanol and reduced with $NaBH_4$. After 2 hours, part of the ethanol is stripped from the reaction mixture, water added, and extracted with ethyl acetate. The extracts are washed with water and then brine, dried over $MgSO_4$, and concentrated. To the solid organic material is added 250 ml of 3N HCl and the mixture refluxed for 3 hours, then extracted with ethyl acetate. The extracts are washed with water and then brine, dried over $MgSO_4$, and concentrated to afford the subtitle compound.

F. 2-methylthio-3-n-hexylcinnamic acid.

To 25 ml of pyridine is added 4.62 g of 2-methylthio-3-n-hexylbenzaldehyde, malonic acid (0.06 mmol) and 0.6 ml of piperidine and the reaction mixture refluxed for 1 hour. After the reaction mixture cools, it is poured over 3N HCl in an ice bath, the solids filtered off, washed with 1N HCl, then dried over $MgSO_4$ to afford the subtitle compound.

G. 2-methylthio-3-n-hexyl-N-hydroxy-N-methylcinnamamide.

To 2-methylthio-3-n-hexylcinnamic acid (1.39 g, 0.005 mmol) in 25 ml of $CH_2Cl_2$ is added oxalyl chloride (0.9, 0.01 mmol) and DMF (0.365 g, 0.005 mmol) with cooling in an ice bath. The bath was removed and the reaction mixture stirred at room temperature for 2 hours to afford 2-methylthio-3-n-hexylcinnamic acid chloride.

To a mixture of 25 ml of THF and 5 ml of water is added methylhydroxylamine hydrochloride salt (1.6 g, 0.02 mmol) and triethylamine (4.0 g, 0.03 mmol).

The acid chloride is added dropwise with the reaction mixture cooling in an ice bath. After stirring at room temperature for 2 hours the reaction mixture is poured into 2N HCl and then extracted twice with $CH_2Cl_2$. The extracts are washed with 1N HCl and then brine, and dried over $MgSO_4$ to afford the subtitle compound.

| Elemental Analysis: | C | H | N |
|---|---|---|---|
| Calculated | 66.41 | 8.20 | 4.56 |
| Found | 66.63 | 8.37 | 4.36 |

EXAMPLE 27

Preparation of 2-(methylthio)-5-(3-phenylpropyl)-N-hydroxy-N-methylcinnamamide.

A. Preparation of 2-(3-bromophenyl)-4,4-dimethyl oxazoline.

To $CHCl_3$ is added 3-bromobenzoic acid (100 g) and thionyl chloride (109 ml) and refluxed overnight. The remaining thionyl chloride is evaporated off to afford 3-bromobenzoic acid chloride.

To 120 ml of methylene chloride is added 2-amino-2-methyl-1-propanol (95 ml) which is then cooled in an ice bath. To this mixture is added, dropwise, 3-bromobenzoic acid chloride in 100 ml of $CH_2Cl_2$ and the reaction mixture stirred for two days. The reaction mixture is filtered and the solids washed with $CH_2Cl_2$. The filtrate and washings are then washed twice with 300 ml portions of water and then with 200 ml of brine and dried over $MgSO_4$.

The resulting solid product is cooled in an ice bath and 2 equivalents of $SOCl_2$ are added and the reaction mixture stirred overnight at room temperature. The mixture is diluted with 1000 ml of diethyl ether and the solids filtered off and washed with diethyl ether. The solids are dissolved in 1N NaOH and extracted twice with 500 ml portions of diethyl ether. The extracts are washed with brine and dried over $MgSO_4$ to afford the subtitle compound.

B. 2[3-(3-phenylpropyl)phenyl]-4,4-dimethyl oxazoline.

Magnesium turnings (10.44 g, .429 mol) are placed in 35 ml of dry THF under argon with iodine crystals. Into 45 ml of dry THF, 3-bromo-1-phenylpropane (65.3 ml, 0.429 mol) is added which is then added to the magnesium turnings until a colorless solution appears. The magnesium suspension is then diluted with 45 ml dry THF and addition of the 3-bromo-1-phenylpropane solution is continued while moderating the temperature in a water bath. After the addition is complete, the reaction mixture is stirred at room temperature for 3 hours.

2-(3-bromophenyl)-4,4-dimethyloxazoline (84.0 g, 0.33 mol) is added to 250 ml of dry THF and then nickel diphenylphosphinoethanedichloride (3.49 g, 0.0066 mol). The Grignard reagent prepared above is placed into an addition funnel by cannula and added dropwise to the oxazoline solution while cooling in an ice bath. The reaction mixture is stirred overnight after the addition is complete.

The reaction mixture is quenched with 100 ml of saturated $NH_4Cl$, then diluted with 300 ml of water. The mixture is then extracted 4 times with 500 ml of diethyl ether. The extracts are washed twice with 250 ml of water, then once with 250 ml of brine and dried over $MgSO_4$. The solids are dissolved in 1000 ml of pentane and filtered, then concentrated to afford the subtitle compound.

C. 2[2-methylthio-5-(3-phenylpropyl)phenyl]-4, 4-dimethyloxazoline.

Into dry THF (230 ml) is placed 2-[3-(3-phenylpropyl)phenyl]-4,4-dimethyloxazoline (20.0 g, 68.1 mmol) which is cooled in an acetonitrile/dry ice bath. To this mixture is added 62.9 ml of 1.3 M s-butyllithium and stirred for 1.5 hours at −40° C. Dimethyldisulfide (7.4 ml, 81.8 mol) is then added and the reaction mixture stirred for 2 hours at −40° C. The reaction mixture is cold quenched with 50 ml of saturated $NH_4Cl$ and allowed to sit overnight. The resulting layers are separated and the aqueous layer extracted twice with 300 ml portions of diethyl ether. The THF layer is washed with brine. The ether layers are then washed with 200 ml of water and then with brine. All organic layers are combined and dried over $MgSO_4$ to afford the subtitle compound.

D. 2-methylthio-5-(3-phenylpropyl)benzoic acid.

The compound 2-[2-methylthio-5-(3-phenylpropyl)-phenyl]-4,4-dimethyloxazoline (24.7 g, 72.7 mmol) is added to 1450 ml of a 4.5 M HCl solution in water and is refluxed overnight. The reaction mixture is extracted twice with 500 ml portions of ethyl acetate. The extracts are washed first with 1 N HCl then once with brine and dried over $MgSO_4$ to afford the subtitle compound.

E. 2-methylthio-5-(3-phenylpropyl)-benzyl alcohol.

$LiAlH_4$ (3.15 g, 82.9 mmol) is suspended in 130 ml of diethyl ether with cooling in an ice bath. 2-methylthio-5-(3-phenylpropyl)benzoic acid (19.8 g, 69.1 mmol) in diethyl ether (50 ml) and dry THF (35 ml) is then added and the reaction mixture stirred at room temperature for 3 hours. The reaction mixture is quenched sequentially with 3.15 ml of water, 3.15 ml of 15% NaOH and 9.45 ml of water. The resulting white precipitate is filtered off and washed thoroughly with diethyl ether. The filtrate and washings are combined and concentrated to afford the subtitle compound.

F. 2-methylthio-5-(3-phenylpropyl)benzaldehyde.

To methylene chloride (150 ml) is added pyridinium dichromate (38.1 g, 101.3 mmol). A solution of 2-methylthio-5-(3-phenylpropyl)-hydroxymethylbenzene (18.4 g, 67.5 mmol) in 20 ml of methylene chloride is then added dropwise to the pyridinium dichromate/$CH_2Cl_2$ suspension. After the addition is completed, the reaction mixture is stirred overnight at room temperature. A further 5 g of pyridinium dichromate is added and the reaction mixture stirred at room temperature overnight. The reaction mixture is filtered through diatomaoceous earth (Celite®) and then through silica gel to afford the subtitle compound.

G. 2-methylthio-5-(3-phenylpropyl)cinnamic acid.

To pyridine (66 ml) is added 2-methylthio-5-(3-phenylpropyl)benzaldehyde (8.92 g, 32.97 mmol), malonic acid (10.29 g, 98.9 mmol) and piperidine (0.98 ml, 9.89 mmol). The reaction mixture is refluxed for 3 hours, then cooled and poured into 2 N HCl. Concentrated HCl is added and the mixture extracted twice with ethyl acetate. The extracts are washed twice with 1N HCl and then brine and dried over $MgSO_2$ to afford the subtitle compound.

H. 2-methylthio-5-(3-phenylpropyl)-N-hydroxy-N-methylcinnamamide.

To dry methylene chloride (32 ml) there is added 2-methylthio-5-(3-phenylpropyl)cinnamic acid (1.0 g, 3.2 mmol). To this mixture is added DMF (0.25 ml, 3.2 mmol) and the reaction mixture cooled in an ice bath. Oxalyl chloride (.61 ml, 7.04 mmol) is slowly added dropwise and the resulting mixture stirred at room temperature for 2 hours to afford 2-methylthio-5-3-phenylpropyl)cinnamic acid chloride in solution.

To THF (15 ml) and water (5 ml) is added methylhydroxyamine hydrochloride (1.07 g, 12.8 mmol) and then triethylamine (2.7 ml, 19.2 mmol). The reaction mixture is cooled in an ice bath and the acid chloride solution is added dropwise. The reaction mixture is stirred overnight at room temperature, and then poured into 2N HCl and extracted twice with $CH_2Cl_2$. The extracts are washed with 1N HCl and then brine and dried over $MgSO_4$ to afford the subtitle compound.

| Elemental Analysis | C | H | N | S |
|---|---|---|---|---|
| Calculated | 70.35 | 6.79 | 4.10 | 9.39 |
| Found | 70.12 | 6.93 | 3.85 | 9.49 |

Mass Spec.: M+(341)

EXAMPLE 31

Preparation of 2-benzylthio-N-hydroxy-N-methylcinnamamide.

By substantially following the procedures described below in Example 33 and using the appropriate reactants, the title compound is afforded.

| Elemental Analysis: | C | H | N |
|---|---|---|---|
| Calculated | 68.20 | 5.72 | 4.68 |
| Found | 67.95 | 5.90 | 4.54 |

EXAMPLE 33

Preparation of 2-(n-butylthio)-N-hydroxy-N-methylcinnamamide.

A. 2-n-butylthiobenzoic acid.

To a solution of thiosalicylic acid (165.8 g, 1.075 mol) in methylethylketone (2900 ml) in a 5 liter flask equipped with a mechanical stirrer is added $K_2CO_3$ (178 g, 1.29 mol) all at once. To this solution is added dropwise a solution of n-butyliodide (217.7 g, 1.18 mol) in about 100 ml of methylethylketone. The reaction is stirred at room temperature for 2 days. The reaction mixture is concentrated in a rotary evaporator and the salt is dissolved in water. The aqueous phase is washed twice with 1000 ml of diethyl ether. The aqueous phase is acidified with 150 ml of concentrated HCl, and extracted twice with ethyl acetate. The extracts are combined and dried over MgSO$_4$ to afford the subtitle compound.

B. 2-(n-butylthio)benzyl alcohol.

Dry diethyl ether (1400 ml) is added to LiAlH$_4$ (24.71 g, 651 mol) which had been cooled in an ice bath. To the mixture 2-n-butylthiobenzoic acid (114.1 g, 0.543 mol) dissolved in 600 ml of dry diethyl ether and 100 ml of THF is added dropwise. The reaction mixture is stirred for 2 hours after the dropwise addition is completed. The mixture is quenched carefully with water (24.7 ml) and then 15% NaOH (24.7 ml) and then water (74 ml). The solids are filtered, and washed with diethyl ether (1000 ml), The filtrate and washings are dried over MgSO$_4$ to afford the subtitle compound.

C. 2-n-butylthiobenzaldehyde.

Pyridinium dichromate (284.6 g, .756 mol) is added to 1100 ml of methylene chloride. The compound 2-(n-butylthio)benzyl alcohol (99.0 g, 0.504 mol) in 160 ml of methylene chloride is added and the mixture stirred at room temperature for 2 days. The mixture is poured into 2000 ml of diethyl ether and filtered through diatomeceous earth (Celite®). The solids are washed extensively with diethyl ether and filtered. The filtrate and washings are combined and washed four times with 1N HCl and then with brine, and dried over MgSO$_4$ to afford the subtitle compound.

D. 2-n-butylthiocinnamic acid.

Malonic acid (80.69 g, .775 mol), 2-n-butyl thiobenzaldehyde (50.22 g, 1258 mol) and piperidine (2.6 ml, 25.8 mol) is added to pyridine (260 ml) and refluxed for 3 hours. The reaction mixture is dripped into cold 1N HCl (1000 ml), then acidified with concentrated HCl. The solids are filtered, then washed with 1N HCl, and dried in vacuo to afford the subtitle compound.

E. 2-(n-butylthio)-N-hydroxy-N-methylcinnamamide.

Methylene chloride (564 ml) is added to 2-n-butylthiocinnamic acid (40.0 g, 0.69 mol) and cooled in an ice bath. To the mixture is added DMF (13.1 ml, 0.169 mol) and then oxalyl chloride (34.0 ml, 0.389 mol) dropwise with the vigorous evolution of gas. After the oxalyl chloride addition is complete, the ice bath is removed and the reaction stirred at room temperature for 2 hours to afford 2-n-butylthiocinnamic acid chloride. Methylhydroxylamine hydrochloride salt (56.5 g, 0.677 mol) is dissolved in THF (50 ml) and water (70 ml) and further THF (96 ml) is added. The acid chloride is added dropwise then stopped so an additional THF (175 ml) and water (35 ml) can be added for solubility. The acid chloride addition is then continued with the reaction mixture being cooled in an ice bath. After the addition is complete, the reaction mixture is stirred at room temperature overnight.

The reaction mixture is poured into 2N HCl (1000 ml) and the resulting layers separated. The aqueous layer is extracted once with chloroform and then the organic layers are washed with 1N HCl and are combined and dried over MgSO$_4$ to afford the subtitle compound.

| Elemental Analysis: | C | H | N | S |
| --- | --- | --- | --- | --- |
| Calculated | 63.37 | 7.22 | 5.29 | 12.08 |
| Found | 63.59 | 7.37 | 5.05 | 11.88 |

Mass Spec.: M+(265)

Example 41

Preparation of 2-(methylsulfinyl)-5-(3-phenylpropyl)-N-hydroxy-N-methylcinnamamide.

In methanol (15 ml) is placed 2-(methylthio)- 5-(3-phenylpropyl)-N-hydroxy-N-methylcinnamamide (0.35 g, 1.02 mmol) prepared according to Example 27 and the solution cooled in an ice bath. In 3 ml of water is placed oxone (0.33 g, 0.533 mmol) which is then added to the cooled methanol solution and stirred for 35 minutes. The reaction mixture is poured into 80 ml of water and extracted twice with 75 ml portions of ethyl acetate. The organic layers are washed with brine and dried over MgSO$_4$ to afford the title compound.

| Elemental Analysis: | C | H | N | S |
| --- | --- | --- | --- | --- |
| Calculated | 67.20 | 6.49 | 3.92 | 8.97 |
| Found | 67.18 | 6.34 | 3.90 | 8.80 |

Mass Spec.: M+ +1(358)

Example 42

Preparation of 2-(methylsulfonyl)-5-(3-phenyl propyl)-N-hydroxy-N-methylcinnamamide.

In methanol (15 ml) is placed 2-methylthio-5-(3-phenylpropyl)-N-hydroxy-N-methylcinnamamide (0.35 g, 1.02 mmol) prepared according to Example 27. In 3 ml of water is placed oxone (0.94 g, 1.54 mmol) which is added to the methanol solution and stirred at room temperature for 3 days. The reaction mixture is poured into 80 ml of water, then extracted twice with 75 ml portions of ethyl acetate. The organic layers are washed with brine and dried over MgSO$_4$ to afford the title compound.

| Elemental Analysis: | C | H | N | S |
| --- | --- | --- | --- | --- |
| Calculated | 64.32 | 6.21 | 3.75 | 8.59 |
| Found | 64.05 | 6.29 | 3.80 | 8.70 |

Mass Spec.: M+(373)

Example 43

Preparation of 2-(3-phenylpropyl)-N-hydroxy-N-methylcinnamamide.

A. 2-(3-phenylpropyl)phenyl-4,4-dimethyloxazoline.

To 130 ml of dry THF is added 2-phenyl-4,4-dimethyloxazoline (2.0 g, 39.95 mmol) which is cooled in a acetonitrile/dry ice bath. To the mixture is slowly added sec-butyllithium (37 ml of 1.3 M) and stirred for 45 minutes. To the mixture is added 7.3 ml 1-phenyl-3-bromopropane. The reaction mixture is stored in a freezer at −10° C. overnight. The reaction mixture is allowed to warm to room temperature and sit overnight.

The reaction mixture is quenched by pouring into 100 ml of saturated NH<Cl, and is extracted twice with 200 ml portions of diethyl ether. The extracts are washed with water then brine, and dried over MgSO to afford the subtitle compound.

By substantially following the procedures described for Example 27, Steps D, E, F, G and H, the compound 2-(3-phenylpropyl)-N-hydroxy-N-methyl cinnamamide is afforded.

| Elemental Analysis: | C | H | N |
|---|---|---|---|
| Calculated | 77.26 | 7.17 | 4.74 |
| Found | 77.40 | 7.16 | 4.86 |

Example 45

Preparation of 2-(methylthio)-5-n-hexyl-N-hydroxy-N-methylcinnamamide.

A. 2-(3-n-hexylphenyl)-4,4-dimethyloxazoline.

To a solution of 2-(3-bromophenyl)-4,4-dimethyloxazoline (104.9 g, 0.413 mol) in dry THF is added nickel diphenylphosphinodichloride (4.5 g). The reaction mixture is placed in a water bath followed by the dropwise addition of the Grignard reagent n-hexylmagnesium bromide in dry THF. The reaction mixture is stirred for 4 hours, then poured into a NH₄Cl solution and extracted with diethyl ether. The organic layer is washed with water and then brine, dried over MgSO₄ and concentrated, then dissolved in hexane and filtered through diatomaceous earth (Celite®) to afford the subtitle compound.

B. 2-(2-methylthio-5-n-hexylphenyl)-4,4-dimethyloxazoline.

To a solution of 2-(3-n-hexylphenyl)-4,4-dimethyloxazoline (21 g, 0.086 mmol) in 200 ml of dry THF is added dropwise, sec-butyllithium (73 ml) at a temperature of −40° C. (dry ice/acetonitrile bath). After stirring one hour at −40° C. a solution of dimethyldisulfide (8.18 g, 0.087 mmol) in THF (7.82 ml) is then added dropwise to the reaction mixture and stirred for 2 hours while keeping the temperature at −40° C. The reaction mixture is poured into saturated NH₄Cl and then extracted with ethyl acetate. The extracts are washed with water and then brine, dried over MgSO₄ and concentrated to afford the subtitle compound.

C. 2-(2-methylthio-5-n-hexylphenyl)-4,4-dimethyloxazoline methiodide.

To a large excess of iodomethane is added 2-(2-methylthio-5-n-hexylphenyl)-4,4-dimethyloxazoline (21 g) and stirred overnight at room temperature. The reaction mixture is concentrated to dryness and hexane added followed by methylethyl ketone. The resulting precipitate filtered off and washed with a solution of hexane/MEK at 4:1, V:V to afford the subtitle compound.

D. 2-methylthio-5-n-hexylbenzaldehyde.

To a solution of the 2-(2-methylthio-5-n-hexyl phenyl)-4,4-dimethyloxazoline methiodide afforded in Reaction C, above, in absolute ethanol at 0° C. is added on equimolar amount of NaBH₄. The reaction mixture is stirred at 10° C. for 2 hours, then concentrated. Water is added and the mixture extracted with ethyl acetate. The extracts are washed with water and then brine, dried over MgSO₄, and concentrated. To the solid organic material is added 250 ml of 3N HCl and the mixture refluxed for 3 hours, then extracted with ethyl acetate. The extracts are washed with water and then brine, dried over MgSO₄, and concentrated to afford the subtitle compound.

E. 2-(methylthio)-5-n-hexylcinnamic acid.

To pyridine (25 ml) is added 2-methylthio-5-n-hexylbenzaldehyde (0.02 mmol), malonic acid (0.06 mmol) and piperidine (0.6 ml) and the mixture heated at reflux for 1 hour. The mixture is cooled, ice added followed by concentrated HCl (10 ml). The reaction mixture is then extracted with ethyl acetate. The extracts are washed with water and then brine, dried over MgSO₄ and concentrated. The solid is dissolved in a minimum of MEK and hexane is added. The solids are filtered, dissolved in methanol and acidified with a few drops of 1N HCl and then dried in vacuo to afford the subtitle compound.

F. 2-(methylthio)-5-n-hexyl-N-hydroxy-N-methyl cinnamamide.

To 25 ml of methylene chloride is added 2-methylthio-5-n-hexylcinnamic acid (1.4 g, 0.005 mmol) with cooling in an ice bath. To this mixture is added DMF (0.365 g, 0.005 mmol) and then oxalyl chloride (0.9 ml, 0.01 mmol) dropwise. The bath is removed and the reaction mixture stirred at room temperature for 2 hours to afford 2-methylthio-5-n-hexylcinnamic acid chloride.

To a mixture of 25 ml of THF and 5 ml of water is added methylhydroxylamine hydrochloride salt (1.6 g, 0.02 mmol) and triethylamine (4 g, 0.03 mmol).

The acid chloride is added dropwise with the reaction mixture cooling in an ice bath and stirred at room temperature overnight. The reaction mixture is poured into 2N HCl and the resulting layers separated. The organic layer is washed once with 1N HCl, the washed with water and then brine, and dried over MgSO₄ to afford the subtitle compound.

| Elemental Analysis: | C | H | N |
|---|---|---|---|
| Calculated | 66.41 | 8.20 | 4.56 |
| Found | 66.67 | 8.24 | 4.80 |

By substantially following the procedures described above one skilled in the art can prepare the compounds of Formula I.

As noted above, the compounds of the present invention are useful for inhibiting the conversion of arachidonic acid by 5-lipoxygenase to 5-hydroperoxy-6, 8, 11, 14-eicosatetraenoic acid (5-HPETE). Therefore, another embodiment of the present invention is a method for inhibiting the conversion of arachidonic acid into leukotrienes which comprises administering to a mammal in need of 5-lipoxygenase inhibition an effective amount of a compound according to Formula I or a pharmaceutically acceptable salt thereof.

The term "effective amount" as used herein, means an amount of a compound of the present invention which is capable of inhibiting the first step of the biochemical synthesis pathway by which arachidonic acid is converted into leukotrienes which is catalyzed by the enzyme 5-lipoxygenase and particularly, inhibiting 5-lipoxygenase. The 5-lipoxygenase inhibition contemplated by the present method includes both medical and/or prophylactic treatment, as appropriate. The specific dose of compound administered according to this invention will, of course, be determined by the particular circumstances surrounding the case, including, for example, the compound administered, the route of administration, and the condition being treated. A typical daily dose will contain from about 0.01 mg/kg to about 20 mg/kg of the active compound of this invention. Preferred daily doses generally will be from about 0.05 to about 10 mg/kg and ideally from about 0.1 to about 5 mg/kg.

The compounds can be administered by a variety of routes including oral, rectal, transdermal, subcutaneous, intravenous, intramuscular, and intranasal. A special feature of the compound of this invention is that they have high potency and therefore lowered dosages are capable of effectively inhibiting the 5-LO catalyzed reaction.

A variety of physiologic functions have been associated with leukotrienes. As such, the compounds of this invention are believed to have the ability to treat in mammals a variety of disorders associated with leukotrienes such as asthma and allergic diseases, inflammatory bowel disease, psoriasis, shock, adult respiratory distress syndrome and arthritis. Therefore, the present invention also provides methods of treating the above disorders at the rates set forth above for the 5-lipoxygenase catalyzed conversion of arachidonic acid to leukotrienes.

The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By pharmaceutically acceptable it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, propylhydroxybenzoates, talc, magnesium stearate and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. "Active ingredient," of course, means a compound according to Formual I or a pharmaceutically acceptable salt thereof.

Formulation 1

Hard gelatin capsules are prepared using the following ingredients:

|  | Quantity (mg/capsule) |
| --- | --- |
| Active Ingredient | 250 |
| starch, dried | 200 |
| magnesium stearate | 10 |
| Total | 40 mg |

The above ingredients are mixed and filled into hard gelatin capsules in 460 mg quantities.

Formulation 2

A tablet is prepared using the ingredients below:

|  | Quantity (mg/capsule) |
| --- | --- |
| Active Ingredient | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| ethanol | 29.75 |
| Propellant 22 | 70.00 |
| (chlorodifluoromethane) |  |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active Ingredient | 60 mg |
| --- | --- |
| starch, | 45 mg |
| microcrystalline cellulose | 35 mg |
| polyvinylpyrrolidone |  |
| (as 10% solution in water) | 4 mg |

| | |
|---|---|
| sodium carboxymethyl starch | 4.5 mg |
| magnesium stearate | 0.5 mg |
| talc | 1 mg |
| Total | 100 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active Ingredient | 80 mg |
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active Ingredient | 225 mg |
| saturated fatty acid glycerides | 2,000 mg |
| Total | 2,225 mg |

The active ingredient is passed through a No. 60 mesh U.S. sieve and suspended in the staturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active Ingredient | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active Ingredient | 100 mg |
| isotonic saline | 1000 ml |

The solution of the above ingredients generally is administered intravenously to a subject at a rate of 1 ml per minute.

The following experiments were carried out to demonstrate the ability of the compounds of the present invention to inhibit 5-lipoxygenase.

5-Lipoxygenase (5-LO) Assay

Ten milliliters of a 2% casein solution is injected intraperitoneally to guinea pigs weighing 250–300 gm. After 16–18 hours, the guinea pigs are killed by suffocation in a carbon dioxide chamber. The peritoneal cavity is infused with 70 ml of saline and 40–50 ml of the fluid is recovered from the cavity. After centrifugation, cell pellets are washed twice in Hank's balanced salt solution (HBSS) without calcium ion.

The cells are then suspended in 5 ml of sodium phosphate buffer, pH 7.1 containing 1 mM, ethylene diamine tetraacetic acid (EDTA), and 0.1% gelatin. About $20$–$30 \times 10^7$ cells are obtained from one guinea pig. Analysis for the cell composition indicated that more than 95 percent of the cells are polymorphonuclear leukocyte (PMNL).

The PMNL suspension is disrupted by five ½-second pulse sonication at the setting of 3 in a Branson Sonifier, Model 350, equipped with a microtip. The sonicates are combined and centrifuged at 30,000 $\times$ g for 10 minutes. The supernatant is kept frozen at $-70°$ C. until use.

Enzyme activity is determined by assaying for 5-hydroxy-6,8,11,14-eicosatetraenoic acid (5-HETE) formation by first incubating 0.2 ml of the supernatant obtained from the PMNL sonicate with the test compound, 1 mM CaCl$_2$, 2 mM ATP, and 1 mM GSH for 5 minutes at 37° C. The mixture is treated with 5 mM $^{14}$C-arachidonic acid and incubated at 37° C. an additional 10 minutes. The enzyme reaction is then stopped by the addition of 10 μl of 1M citric acid and 10 μl of an alcohol solution containing 20 mg/ml each of indomethacin and butylated hydroxyanisole (BHA). The reaction mixture is spotted (50 μl) on a silica gel plate (Baker TLC plate S1250-PA-19C) and subjected to TLC in a solvent system of ethyl acetate/2,2,4-trimethylpentane/glacial acetic acid/H$_2$O (90:50:20:100).

The radioactivity of the arachidonic acid and its metabolites (5-HETE and LTB$_4$) is visualized from a developed x-ray film which had been exposed to the TLC plate 1–2 days. The amount of 5-HETE formed is quantitated by scraping the silica gel area corresponding to the spot on the x-ray film, and the radioactivity determined in a Isocap/300 liquid scintillation counter (Searle Analytic, Inc.).

The percent inhibition of the formation of 5-HETE is determined for each concentration of compound tested as compared to a control experiment wherein no test compound is added. The concentration and percent values are plotted on semi log paper and the concentration in which formation of 5-HETE is inhibited by 50%

($IC_{50}$) is determined by interpolation. The results are set forth in Table II.

H-PMN Assay

Sodium citrated venous blood is drawn from normal human subjects. After centrifugation at 300 ×g for 15 minutes, the platelet-rich layer of plasma is discarded and an equal volume of Hanks' balanced salt solution (HBSS) is added to the enriched cell fraction. This platelet-depleted cell suspension is then layered on an equal volume of Ficoll-Paque. After centrifugation for 40 minutes at 300 ×g, the bottom layer containing erythrocytes and polymorphonuclear leukocytes (PMNs) is diluted with two volumes of a 0.2% methocel solution. The erythrocytes are sedimented upon standing for 15 minutes, and the supernatant containing the PMNs is aspirated and centrifuged at 300 ×g, for 5 minutes. The cell pellet is then exposed to 0.2% NaCl for 30 seconds to lyse any remaining erythrocytes, and the ionic strength of the suspension is readjusted to 0.9% with NaCl. The PMNs are recovered by centrifugation at 300 ×g for 5 minutes and are suspended in HBSS to a concentration of $2 \times 10^6$ cells/ml.

The test compounds are dissolved in and diluted with dimethylsulfoxide (DMSO) which also contains $2 \times 10^{-6}$M of the calcium ionophore, A23187. To 1 ml of the PMN suspension, 10 μl of the DMSO solution is added, and the mixture is incubated at 37° C. for 10 minutes. The PMNs are rapidly pelleted in a microcentrifuge, and the supernatant is kept at −20° C. for future determination of $LTB_4$ content via the radioimmunoassay.

TABLE II

| Example No. | μM 5-LO | μM H-PMN |
|---|---|---|
| 1 | — | — |
| 2 | .044 | .012 |
| 3 | .017 | .009 |
| 4 | .072 | .075 |
| 5 | .032 | .024 |
| 6 | .007 | — |
| 7 | .024 | — |
| 8 | .023 | — |
| 9 | .09 | .259 |
| 10 | .097 | .118 |
| 11 | .096 | .071 |
| 12 | .695 | — |
| 13 | .023 | — |
| 14 | .031 | — |
| 15 | .490 | — |
| 16 | .074 | — |
| 17 | .059 | .150 |
| 18 | .175 | — |
| 19 | .082 | .025 |
| 20 | .459 | .190 |
| 21 | .166 | .461 |
| 22 | .148 | .204 |
| 23 | .392 | .10 |
| 24 | .131 | — |
| 25 | .014 | — |
| 26 | .014 | — |
| 27 | .026 | .018 |
| 28 | .008 | — |
| 29 | .094 | .058 |
| 30 | .059 | .046 |
| 31 | .033 | .007 |
| 32 | 8.40 | — |
| 33 | .047 | .022 |
| 34 | 1.10 | — |
| 35 | .009 | .016 |
| 36 | 2.440 | — |
| 37 | .053 | .028 |
| 38 | .028 | .011 |
| 39 | .033 | — |
| 40 | .052 | .017 |
| 41 | .160 | — |
| 42 | .304 | — |
| 43 | .060 | .012 |
| 44 | .031 | .017 |
| 45 | .058 | .02 |

Certain compounds specifically disclosed or within the scope of the known hydroxamic acid derivatives have been evaluated in one or both of the abovedescribed assays. As with the evaluations above, the percent inhibition of the formation of 5-HETE was determined for each concentration of compound tested as compared to a control experiment wherein no test compound was added. The concentration and percent inhibition values are plotted on semi log paper and the concentration in which formation of 5-HETE is inhibited by 50% ($IC_{50}$) is determined by interpolation. The results of these evaluations are presented below in Table III along with the structure of the compound being evaluated.

TABLE II

| Example No. | Structure | μM 5-Lo | μM H-PMN |
|---|---|---|---|
| A | 2-(methylthio)-N-methyl-benzohydroxamic acid | 44 | — |
| B | (2-methoxycinnamoyl)-N-methylhydroxamic acid | 1.2 | .143 |
| C | 2-(methylthio)-6-(3-phenylpropyl)-N-methyl-benzohydroxamic acid | .592 | — |
| D | 2-(butylthio)-6-(3-phenylpropyl)-N-methyl-benzohydroxamic acid | .178 | .440 |
| E | 2-ethyl-6-(3-phenylpropyl)-N-methyl-benzohydroxamic acid | .550 | — |

TABLE II-continued

| Example No. | | μM 5-Lo | μM H-PMN |
|---|---|---|---|
| F | OH<br>\|<br>O=C—N—CH₃<br>\|<br>CH<br>\|\|<br>CH<br>(2-O-CH₂-phenyl on phenyl) | .054 | .042 |
| G | OH<br>\|<br>O=C—N—CH₃<br>\|<br>CH<br>\|\|<br>CH<br>(2-O-(CH₂)₃—CH₃ on phenyl) | .041 | .052 |

Compound A includes a 2-methylthio substituent on the phenyl ring but is a benzoic acid derivative rather than a cinnamic acid derivative. Compound B in a cinnamic acid derivative but includes a 2-methoxy substituent rather than a 2-methylthio substituent. Example 23 of the present invention is a 2-methoylthio cinnamic acid derivative.

Compound C is a benzoic acid derivative containing the same ring substituents as Example 27 which is a cinnamic acid derivative.

Compounds D and E are both benzoic acid derivatives containing the same ring substitutents as, respectively, Examples 29 and 30 which are cinnamic acid derviatives.

Compound F is a cinnamic acid derivative but includes a 2benzyloxy substituent rather than a 2-benzylthio substituent as in Example 31 of the present invention.

Compound G is a cinnamic acid derivative but includes a 2-butoxy substituent rather than a 2-butylthio substituent as in Example 33 of the present invention.

It should be understood that the instant specification and examples are set forth by way of illustration and not limitation, and that various modifications and changes may be made without departing from the spirit and scope of the present invention as defined by the appended claims.

We claim:

1. A 2(substituted)-N-hydroxy-N-alkyl-cinnamamide of the formula

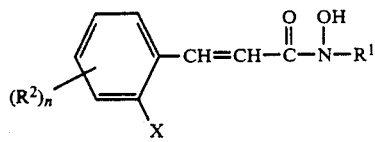   I where
R¹ is C₁-C₄ alkyl;
n is 0 or 1;
R² is trifluoromethyl, phen(C₁-C₄)-alkylene or

where
m is 0, 1, or 2, and
R³ is C₁-C₄ alkyl;
X is phenyl, phen(C₁-C₄)alkylene where the phenyl ring is unsubstituted or monosubstituted with —S-(O)ₘ—R³ and m and R³ are as defined above, or

where
m is 0, 1, or 2, and
R⁴ is C₂-C₁₂ alkenyl, C₂-C₁₂ alkynyl, or unsubstituted or monosubstituted C₁-C₂₀ alkyl where the substituent is CF₃, C₃-C₈ cycloalkyl, or phenyl, or a pharmaceutically acceptable salt thereof.

2. A compound according to claim 1 wherein:
R¹ is C₁-C₃ alkyl;
n is 0 or 1;
R² is CF₃, phen(C₁-C₄)alkylene or —S—R³ and R³ is C₁-C₄ alkyl;
x is phen(C₁-C₄)alkylene, where the phenyl ring is unsubstituted or S—R⁴ and R⁴ is C₃-C₆ alkenyl, unsubstituted or substituted C₁-C₁₀ alkyl where the substituent is CF₃, C₅-C₆ cycloalkyl, or phenyl, or a pharmaceutically acceptable salt thereof.

3. A compound according to claim 2 wherein:
R¹ is methyl or isopropyl;
n is 0 or 1;
R² is a 4- or 3-position CF₃, phen(C₁-C₃) alkylene or —S—R³ where R³ is c₁-C₃ alkyl;
X is phen(C₁-C₃)alkylene or —S—R⁴ where R⁴ is C₃-C₆ alkenyl, unsubstituted or substituted C₁-C₁₀ alkyl where the substituent is CF₃, cyclohexyl, or phenyl, or a pharmaceutically acceptable salt thereof.

4. A compound according to claim 3 wherein:
R¹ is methyl or isopropyl;
n is 0 or 1;
R² is a 4-position phen(C₁-C₃)alkylene;
X is —S—R⁴ where R⁴ is unsubstituted or substituted C₁-C₈ alkyl where the substituent is phenyl, or a pharmaceutically acceptable salt thereof.

5. A compound according to claim 4 wherein said compound is 2-n-hexylthio-N-hydroxy-N-methylcinnamamide or a pharmaceutically acceptable salt thereof.

6. A compound according to claim 4 wherein said compound is 2-methylthio-4-(3-phenylpropyl)-N-hydroxy-N-methylcinnamamide or a pharmaceutically acceptable salt thereof.

7. A compound according to claim 4 wherein said compound is 2-n-butylthio-N-hydroxy-N-isopropylcinnamamide or a pharmaceutically acceptable salt thereof.

8. A compound according to claim 4 wherein said compound is 2-benzylthio-N-hydroxy-N-methylcinnamamide or a pharmaceutically acceptable salt thereof.

9. A pharmaceutical composition comprising a pharmaceutically acceptable carrier, diluent or excipient and an effective amount of a compound having the formula

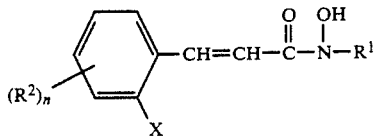

where
R$^1$ is C$_1$-C$_4$ alkyl;
n is 0 or 1;
R$^2$ is trifluoromethyl, phen(C$_1$-C$_4$)alkylene or

where m is 0, 1 or 2 and R$^3$ is C$_1$-C$_4$ alkyl;
X is phenyl, phen(C$_1$-C$_4$)alkylene where the phenyl ring is unsubstituted or monosubstituted with —S(O)$_m$—R$^3$ and m and R$^3$ are as defined above, or

where m is 0, 1 or 2 and R$^4$ is C$^2$-C$^{12}$ alkenyl, C$_2$-C$_{12}$ alkynyl, unsubstituted or monosubstituted C$_1$-C$_{20}$ alkyl where the substituent is CF$_3$, C$_3$-C$_8$ cycloalkyl, or phenyl, or a pharmaceutically acceptable salt thereof.

10. A pharmaceutical composition according to claim 9 wherein:
R$^1$ is C$_1$-C$_3$ alkyl;
n is 0 or 1;
R$^2$ is CF$_3$, phen(C$_1$-C$_4$)alkylene or —S—R$^3$ and R$^3$ is C$_1$-C$_4$ alkyl;
X is C$_3$-C$_6$ alkyl, phen(C$_1$-C$_4$)alkylene, where the phenyl ring is unsubstituted or S—R$^4$ is C$_3$-C$_6$ alkenyl, unsubstituted or substituted C$_1$-C$_{10}$ alkyl where the substituent is CF$_3$, C$_5$-C$_6$ cycloalkyl, or phenyl, or a pharmaceutically acceptable salt thereof.

11. A pharmaceutical composition according claim 10 wherein:
R$_1$ is methyl or isopropopyl;
n is 0 or 1;
R$^2$ is a 4- or 3-position CF$_3$, phen(C$_1$-C$_3$)alkylene or —S—R$^3$ where R$^3$ is C$_1$-C$_3$ alkyl;
X is phen(C$_1$-C$_3$)alkylene or —S—R$^4$ where R$^4$ is C$_3$-C$_6$ alkenyl, unsubstituted or substituted C$_1$-C$_{10}$ alkenyl, unsubstituted or substituent is CF$_3$, cyclohexyl, or phenyl, or a pharmaceutically acceptable salt thereof.

12. A pharmaceutical composition according to claim 11 wherein:
R$^1$ is methyl or isopropyl:
n is 0 or 1;
R$^2$ is a 4-position phen(C$_1$-C$_3$)alkylene;
x is —S—R$^4$ where R$^4$ is unsubstituted or substituted C$_1$ -C$_8$ alkyl where the substituent is phenyl, or a pharmaceutically acceptable salt thereof.

13. A pharmaceutical composition according to claim 12 wherein said compound is 2-n-hexylthio-N-hydroxy-N-methylcinnamide or a pharmaceutically acceptable salt thereof.

14. A pharmaceutical composition according to claim 12 wherein said compound is 2-methylthio-4-(3-phenyl-propyl)-N-hydroxy-N-methylcinnamamide or a pharmaceutically acceptable salt thereof.

15. A pharmaceutical composition according to claim 12 wherein said compound is 2-n-butylthio-N-hydroxy-N-isopropylcinnamamide or a pharmaceutically acceptable salt thereof.

16. A pharmaceutical composition according to claim 12 wherein said compound is 2-benzylthio-N-hydroxy-N-methlycinnamamide or a pharmaceutically acceptable salt thereof.

17. A method of inhibiting 5-lipoxygenase comprising administering to a mammal in need of 5-lipoxygenase inhibition an effective amount of a compound of the formula

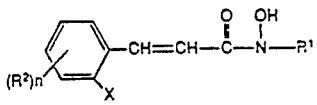

where
R$^1$ is C$_1$-C$_4$ alkyl;
n is 0 or 1;
R$^2$ is trifluoromethyl, phen(C$_1$-C$_4$)alkylene or

where m is 0, 1 or 2 and R$^3$ is C$_1$-C$_4$ alkyl;
X is phenyl, phen(C$_1$-C$_4$)alkylene where the phenyl ring is unsubstituted or monosubstituted with —S()$_m$—R$^3$ and m and R$^3$ are as defined above, or

where m is 0, 1 or 2 and R$^4$ is C$^2$-C$^{12}$ alkenyl, C$^2$-C$^{12}$ alkynyl, or unsubstituted or monosubstituted C$_1$-C$_{20}$ alkyl where the substituent is CF$_3$, C$_3$-C$_8$ cycloalkyl, or phenyl, or a pharmaceutically acceptable salt thereof.

18. A method according to claim 17 wherein:
R$^1$ is C$_1$-C$_3$ alkyl;
n is 0 or 1;
R$^2$ is CF$_3$, phen(C$_1$-C$_4$)alkylene or —S—R$^3$ and R$^3$ is C$_{1-4}$ alkyl;
X is phen(C$_1$-C$_4$)alkylene, where the phenyl ring is unsubstituted or S—R$^4$ and R$^4$ is C$_3$-C$_6$ alkenyl, unsubstituted or substituted C$_1$-C$_{10}$ alkyl where the substituent is CF$_3$, C$_5$-C$_6$ cycloalkyl, or phenyl, or a pharmaceutically acceptable salt thereof.

19. A method according to claim 18 wherein:
R$^1$ is methyl or isopropyl:
n is 0 or 1;
R$^2$ is a 4-position phen(C$_1$-C$_3$)alkylene;
X is —S—R$^4$ where R$^4$ is unsubstituted or substituted C$_1$-C$_8$ alkyl where the substituent is phenyl, or a pharmaceutically acceptable salt thereof.

20. A method according to claim 19 wherein:
R$^1$ is methyl or isopropyl;
n is 0 or 1;
R$^2$ is a 4-position phen(C$_1$-C$_3$)alkylene;
X is —S—R$^4$ where R$^4$ is unsubstituted or substituted C$_1$-C$_8$ alkyl where the substitutent is phenyl, or a pharmaceutically acceptable salt thereof.

21. A method according to claim 20 wherein said compound is 2-n-hexylthio-N-hydroxy-N-methylcinnamamide or a pharmaceutically acceptable salt thereof.

22. A method according to claim 20 wherein said compound is 2-methylthio-4-(3-phenylpropyl)-N-hydroxy-N-methylcinnamamide or a pharmaceutically acceptable salt thereof.

23. A method according to claim 20 wherein said compound is 2-n-butylthio-N-hydroxy-N-isopropylcinnamamide or a pharmaceutically acceptable salt thereof.

24. A method according to claim 20 wherein said compound is 2-benzylthio-N-hydroxy-N-methylcinnamamide or a pharmaceutically acceptable salt thereof.

* * * * *

UNITED STATES PATENT AND TRADEMARK OFFICE
CERTIFICATE OF CORRECTION

PATENT NO. : 5,028,629

DATED : July 2, 1991

INVENTOR(S) : Hite, et al.

It is certified that error appears in the above-identified patent and that said Letters Patent is hereby corrected as shown below:

Claim 1 at column 29, line 51, "2(substituted)-" should read -- 2-(substituted)- --.

Claim 9 at column 31, line 27, "$C^2-C^{12}$ alkenyl," should read -- $C_2-C_{12}$ alkenyl, --.

Claim 10 at column 31, line 37, "X is $C_3-C_6$ alkyl, phen($C_1-C_4$)alkylene, should read -- X is phen($C_1-C_4$)alkylene, --.

Claim 17 at column 32, line 31, "$-S(\,)_m-R^3$" should read -- $-S(O)_m-R^3$ --.

Claim 17 at column 32, line 38, "$C^2-C^{12}$ alkenyl," should read -- $C_2-C_{12}$ alkenyl, --.

Claim 17 at column 32, line 39, "$C^2-C^{12}$ alkynyl," should read -- $C_2-C_{12}$ alkynyl, --.

Signed and Sealed this

Thirteenth Day of April, 1993

Attest:

STEPHEN G. KUNIN

*Attesting Officer*     *Acting Commissioner of Patents and Trademarks*